(12) United States Patent
Dasani et al.

(10) Patent No.: US 7,561,665 B2
(45) Date of Patent: Jul. 14, 2009

(54) DUAL PULSE IMAGING

(75) Inventors: Govin Dasani, Epsom (GB); Wolfgang Kaissl, Wil/ZH (CH); Evangelos Matsinos, Untersiggenthal (CH); Daniel Morf, Buch am Irchel (CH); Heinrich Riem, Baden-Daettwil (CH)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

(21) Appl. No.: 11/406,570

(22) Filed: Apr. 18, 2006

(65) Prior Publication Data

US 2007/0081628 A1   Apr. 12, 2007

Related U.S. Application Data

(60) Provisional application No. 60/724,667, filed on Oct. 7, 2005.

(51) Int. Cl.
*G01N 23/04* (2006.01)

(52) U.S. Cl. ...................... 378/62; 378/98.9

(58) Field of Classification Search ............. 378/62, 378/98, 98.8, 98.9, 98.11, 98.12; 382/132, 382/270, 272, 274
See application file for complete search history.

(56) References Cited

U.S. PATENT DOCUMENTS

| | | | |
|---|---|---|---|
| 6,040,858 A * | 3/2000 | Ikeda | 348/242 |
| 6,683,934 B1 * | 1/2004 | Zhao et al. | 378/9 |
| 6,800,858 B1 | 10/2004 | Seppi | |
| 6,868,138 B2 * | 3/2005 | Clinthorne et al. | 378/98.8 |
| 7,103,143 B2 * | 9/2006 | Alving et al. | 378/98.7 |
| 2006/0056581 A1 * | 3/2006 | Hoffman et al. | 378/19 |
| 2007/0076842 A1 * | 4/2007 | Tkaczyk et al. | 378/5 |

* cited by examiner

*Primary Examiner*—Jurie Yun
(74) *Attorney, Agent, or Firm*—Houst Consulting (57) ABSTRACT

A dual pulse imaging method is provided comprising the steps of generating a first image of a region of interest by a first pulse delivering a first dose, generating a second image of the region of interest by a second pulse delivering a second dose different from the first dose, and computing a third image of the region of interest using data from the first and second images. A threshold can be identified for determining data from the first and second images to be used in computing the third image. A dual pulse imaging system is also provided.

11 Claims, 6 Drawing Sheets

DUAL PULSE IMAGING

CROSS REFERENCES TO RELATED APPLICATIONS

This application claims the benefit of priority under 35 U.S.C. § 119(e) to U.S. provisional patent application Ser. No. 60/724,667 entitled "Dual Pulse Imaging" filed Oct. 7, 2005, the disclosure of which is incorporated herein by reference.

FIELD OF THE INVENTION

This invention relates generally to radiographic imaging, and in particular to dual pulse imaging methods and systems that enhance the dynamic range of radiographic images.

BACKGROUND

Radiographic imaging such as x-ray imaging has been used for a wide variety of applications in various fields. A typical x-ray imaging system includes an x-ray source generating x-ray beams to irradiate a region of interest (ROI), and an x-ray detector detecting the x-ray beams passing through the ROI. For applications such as radiotherapy, the ability to view a region of interest within a dense anatomy such as tumor as well as the body contour is necessary for exact treatment of the tumor while sparing healthy surrounding tissue. However, the dynamic range of signals of images can limit the ability to view both of these areas. One problem of prior art methods of using high x-ray intensity for imaging thick or dense tissue is that the body contour (such as the area near the skin surface) can be saturated in the images, and as a result, no useful information can be discerned.

Accordingly, there is a need for improving the design, construction and operation of radiographic systems to enhance the dynamic range of signals in the images produced by the systems. There is a need for an imaging method that can provide good image contrast over a wide range of body thickness for accurate diagnosis and positioning for treatment.

SUMMARY OF THE INVENTION

A dual pulse imaging method is provided comprising the steps of generating a first image of a region of interest by a first pulse delivering a first dose, generating a second image of the region of interest by a second pulse delivering a second dose different from the first dose, and computing a third image of the region of interest using data from the first and second images. A threshold can be identified for determining where to use data from the first and second images to compute the third image.

In some embodiments, the dual pulse imaging method is performed using an imager having a plurality of pixels. The first and second images are generated by the imager. A threshold is identified by determining the signal value above which the second image saturates.

In some embodiments, the third image is computed by using data from the second image for pixels unsaturated by the second pulse, and using data from the first image for pixels saturated by the second pulse. The data from the first image is scaled by an optimal ratio.

A dual imaging system is also provided comprising an X-ray source driven in such a way as to generate a first pulse delivering a first dose and a second pulse delivering a second dose different from the first dose, a detector generating a first image representative of the first pulse passing through a region of interest and a second image representative of the second pulse passing through the region of interest, a memory storing the first and second images, and a processor processing the first and second images and computing a third image using data from the first and second images. In some embodiments, the third image is computed by using data from the second image for pixels unsaturated by the second pulse and using data from the first image for pixels saturated by the second pulse. The data from the first image may be scaled by an optimal ratio of signals corresponding to the second and first pulses for pixels unsaturated by the second pulse.

In some embodiments, the energy source is an x-ray generator that may be driven in such a way as to generate x-ray corresponding to different energy levels and intensity. The detector can be an imager having a plurality of pixels.

BRIEF DESCRIPTION OF THE DRAWINGS

These and various other features and advantages of the present invention will become better understood upon reading of the following detailed description in conjunction with the accompanying drawings and the appended claims provided below, where:

DETAILED DESCRIPTION OF THE INVENTION

Various embodiments of the present invention are described hereinafter with reference to the figures. It should be noted that the figures are only intended to facilitate the description of specific embodiments of the invention. They are not intended as an exhaustive description of the invention or as a limitation on the scope of the invention. In addition, an aspect described in conjunction with a particular embodiment of the present invention is not necessarily limited to that embodiment and can be practiced in any other embodiments of the present invention. For instance, in the following description, the present invention is described with embodiments of an x-ray imaging system. It will be appreciated that the claimed invention can also be used for other imaging systems which require a wide dynamic range. Further, in the following description, the present invention is described with embodiments of radiotherapy. It will be appreciated that the claimed invention can be used in other applications, including but not limited to security inspection.

Figure 1:
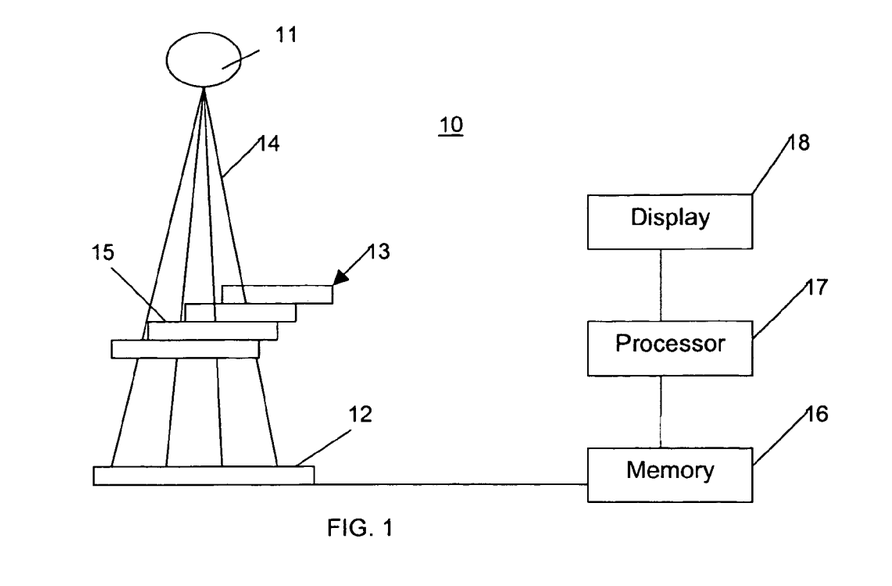
FIG. 1 is a schematic diagram illustrating an imaging system in accordance with one embodiment of the present invention.

FIG. 1 illustrates an x-ray imaging system 10 in accordance with one embodiment of the present invention. The x-ray imaging system 10 includes an x-ray source 11 and a detector 12. Between the x-ray source 11 and detector 12 is an object 13 to be examined. The object 13 under examination may be a human patient, test phantom, or any other item or region of interest to be examined. The x-ray source 11 may be an x-ray tube. The detector 12 may be a flat panel solid state image detector. For example, the detector may be comprised of semiconductor Field Effect Transistors (FETs) and photodiodes forming a plurality of cells or pixels in a two dimensional panel. U.S. Pat. No. 6,800,858 discloses an x-ray image detecting device that is capable of detecting multiple energy level x-ray images and can be used as detector in accordance with the present invention. U.S. Pat. No. 6,800,858 is incorporated herein by reference in its entirety.

The x-ray source 11 generates and emits an x-ray beam 14 to a region of interest 15 in the object 13. The x-ray detector 12 receives and detects the x-ray beam passing through the region of interest 15. The x-ray beam 14 is converted to electrical signals (pixel values) representing the intensity of the x-ray beams passing through the region of interest 15.

The x-ray imaging system 10 includes a memory 16 coupled to the detector 12 for receiving electrical signals from the detector 12 and storing images computed by a processor. The memory 16 may also store a computer program including algorithms or instructions executed by a processor. The memory may include hard disks, floppy disks, CDROMs, etc. and may store both low dose level images and high dose level images. A processor 17 is coupled to the memory 16 to process and generate image data according to the methods described herein. The processor 17 can be a microcontroller, microprocessor, custom ASIC, and the like. A display device 18 is coupled to the processor 17 to display images generated by the processor 17.

Referring to FIGS. 2-7, a dual pulse imaging method according to one embodiment of the present invention will now be described. In general, two pulses of x-ray are sequentially emitted to the region of interest 15 to generate two images. The first pulse is preferably chosen such that low attenuating tissue can be imaged whereas the second pulse is preferably chosen to image thick or highly attenuating tissues. An implemented algorithm then combines the data from both images on a pixel-by-pixel basis to generate a third image with high contrast in all regions.

Figure 2:
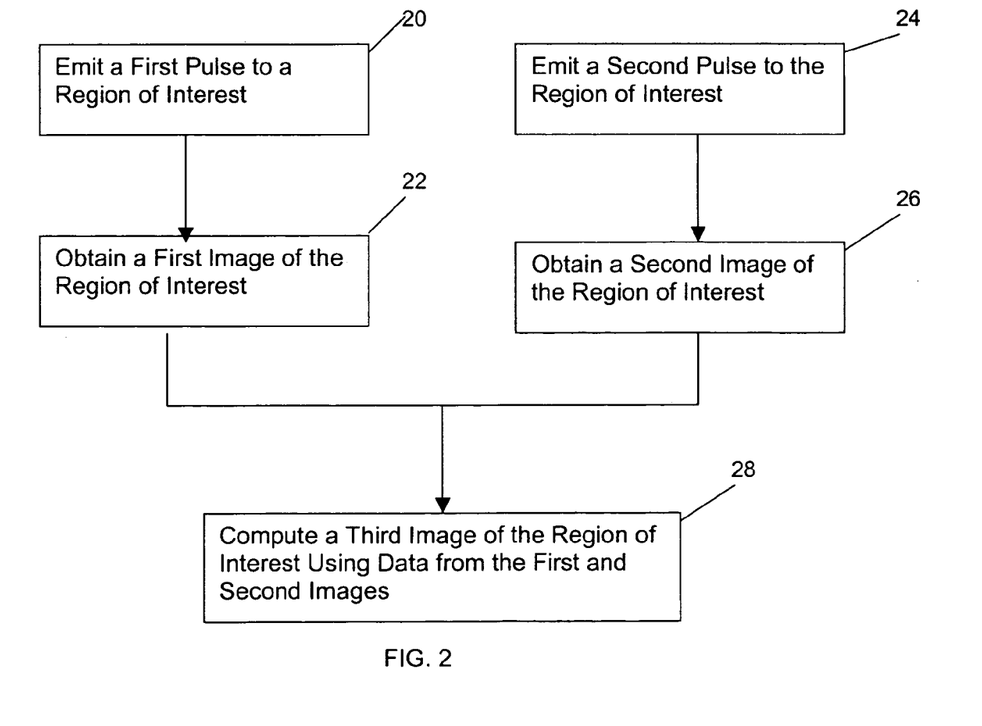
FIG. 2 is a flowchart illustrating exemplary steps of the dual pulse imaging method in accordance with one embodiment of the present invention.

FIG. 2 is a flowchart showing an exemplary dual pulse imaging method that can be performed by the imaging system 10. At step 20, a first pulse of x-ray beam is emitted to the region of interest 15. In some embodiments, the first pulse delivers a low dose of x-ray so that the background of the region of interest 15 is not saturated in the image processed. As used herein, "saturation" in images refers to the state that any increase in the dose delivered by X-ray is not accompanied by a (linear) increase in the signal produced at the output, i.e., the dose-signal linearity is not fulfilled in the pixels that are saturated. A first image of the region of interest 15 is obtained by the first pulse at step 22.

At step 24, a second pulse of x-ray is emitted to the region of interest 15. In some embodiments, the second pulse delivers a high dose of x-ray to image a high attenuating tissue in the region of interest. A second image of the region of interest 15 is obtained by the second pulse at step 26. Generally, a higher dose generates a brighter image of the region of interest. In some embodiments, the second image generated by the second pulse of a higher dose may cause some detector pixels to saturate and as a result, useful information cannot be discerned solely from the second image. An algorithm as will be described in more detail below can be used to combine the data from both the first and second images to compute a combined or third image with high contrast in all regions.

The low or high doses delivered by the first and second pulses may correspond to different system parameters such as x-ray tube voltages (kVp) and exposures (mAs) and can be optimized for specific applications. The optimization of parameters can be based on variables provided by the user such as patient size and specific region of interest or obtained by the system by such as collecting single images for different voltages and exposures etc. By way of example, the energy level of doses may range from 50 to 150 kVp and exposure can range from 0.1 mAs to 630 mAs. In some embodiments, filters may be used for greater separation of x-ray energies.

In some embodiments, two successive images are obtained from the first and second pulses within a minimum time in between to reduce artifacts. By way of example, the time between the first and second pulses can be approximately 100 milliseconds.

Returning to FIG. 2, once the first and second images are obtained by the first and second pulses, the flow proceeds to step 28 where a third image is computed by using the data from both the first and second images.

Figure 3:
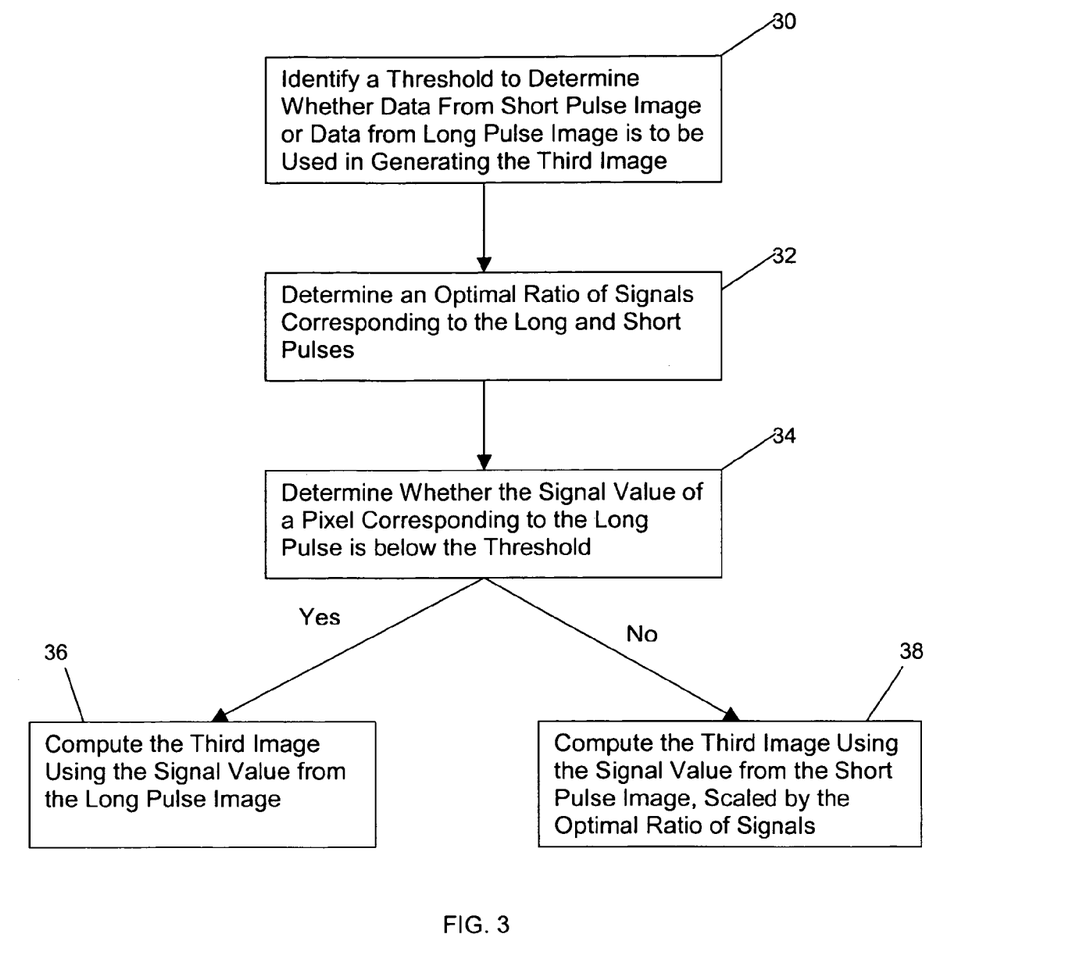
FIG. 3 is a flowchart illustrating exemplary steps for generating a combined image in accordance with one embodiment of the present invention.

FIG. 3 is a flowchart illustrating exemplary steps for computing a third image of the region of interest using data from the first and second images. At step 30, a threshold is identified that determines whether the data from the first image or the data from the second image is to be used in computing the third image. An optimal ratio of signals corresponding to the long and short pulses is determined at step 32. In some embodiments, the optimal ratio is the average of the signal ratio distribution for pixels unsaturated by the long pulse dose. At step 34, the signal value of a pixel corresponding to the long pulse dose is compared to the threshold as identified at step 30. If the pixel value is below the threshold, then the flow proceeds to step 36 where the pixel value from the long pulse image is used to compute the third image. If the pixel value is above the threshold, then the flow proceeds to step 38 where the pixel value from the short pulse image, scaled by the optimal ratio as determined at step 32, is used to compute the third image.

Figure 4:
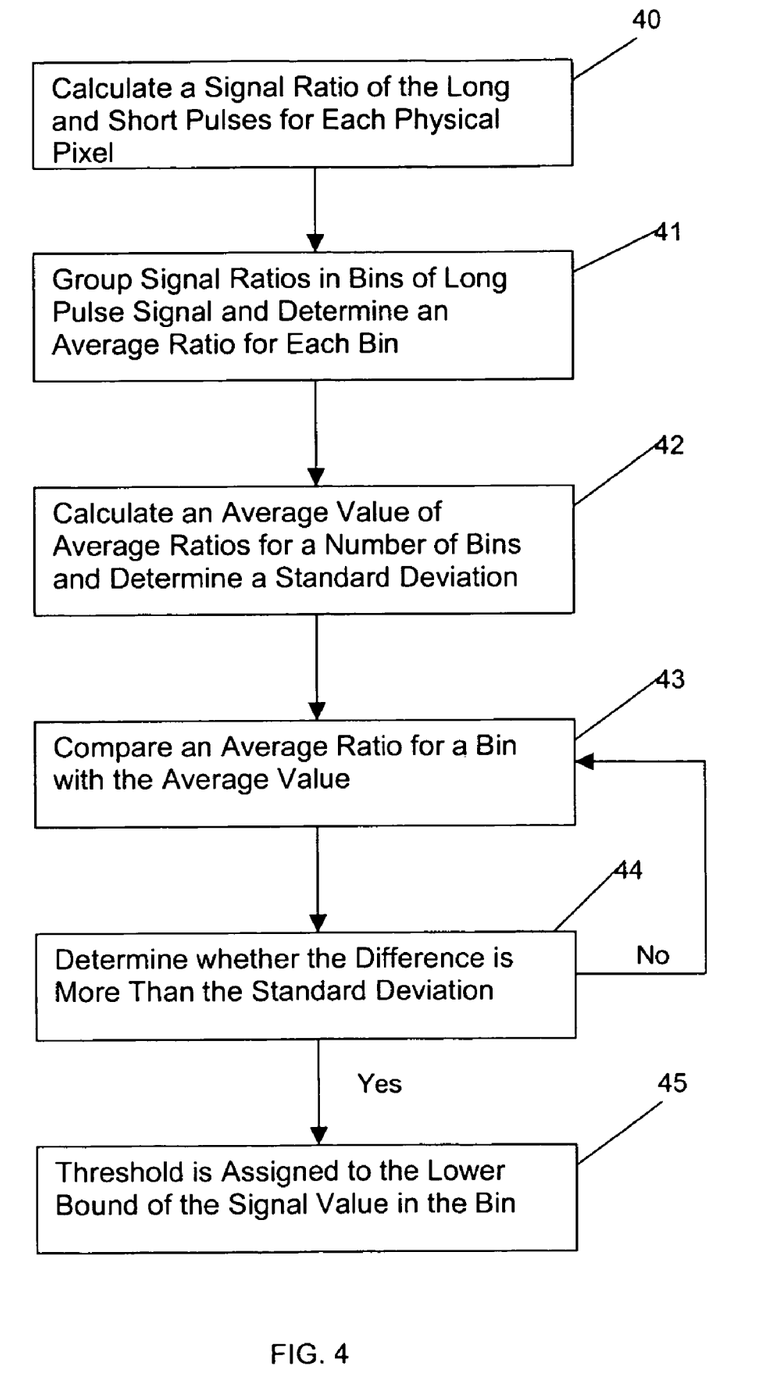
FIG. 4 is a flowchart illustrating exemplary steps for determining a signal threshold in accordance with one embodiment of the present invention.

FIG. 4 is a flowchart illustrating exemplary steps for determining the threshold where the data from the short pulse image or the data from the long pulse image is to be used in computing the third image. At step 40, the signal ratio of long and short pulses to each physical pixel is calculated. At step 41, the signal ratios calculated at step 40 are grouped or histogrammed in bins of the long pulse signal and an average ratio in each histogram bin is determined. Then the flow proceeds to step 42 where an average value of signal ratios for a number of bins is calculated and a standard deviation is determined. By way of example, the average ratios of ten bins can be used in calculation of the first average value and standard deviation. At step 43, an average ratio in a particular bin is compared with the average value obtained at step 42. If the difference between the average ratio in the particular bin and the average value is within for example five times the standard deviation as determined at step 44, then the current bin is included in the calculation of a new overall average and the new overall standard deviation and the flow returns to step 43 to compare the average ratio in the subsequent bin with the average value. If the difference between the average ratio of a particular bin and the average value is more than for example five times the standard deviation, then the flow proceeds to step 45 where the threshold is assigned to the lower bound of the signal value of the particular bin that was tested for constancy of the signal ratio derivative.

Figure 5:
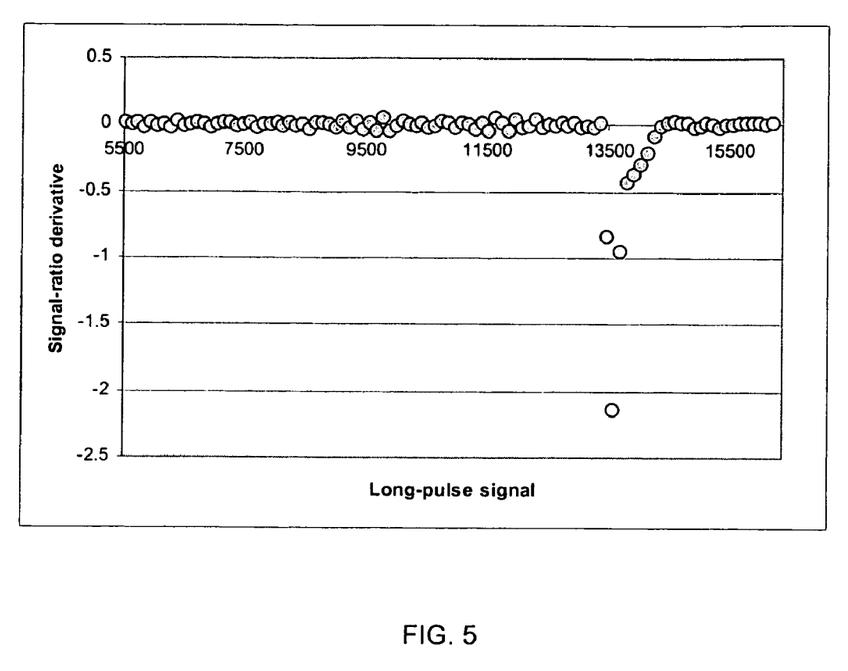
FIG. 5 is a plot showing signal ratio derivatives with respect to long pulse signals in accordance with one embodiment of the present invention.

FIG. 5 illustrates an exemplary embodiment of the present invention for determining the threshold. FIG. 5 is a plot of derivatives of signal ratios of long and short pulses with respect to the long pulse signal. As illustrated in FIG. 4, the signal ratio of long and short pulses for each physical pixel is firstly calculated and then histogrammed in bins of the long pulse signal. An average ratio is obtained in each histogram bin. The derivative of the average ratio distribution, i.e., the difference of the average ratio contained in neighboring bins of the histogram is shown in FIG. 5. One advantage of using derivative of signal ratios is the riddance of a possible slope effects in the original histogram and greater sensitivity in the area where the signal ratio departs from constancy. The threshold is obtained from the derivative plot as follows. Assume that an average and a standard deviation such as root means square of values on the derivative plot have been calculated from a number of bins. The contents of the subsequent bin are tested for constancy in terms of the current average and deviation. In case the absolute value of the difference of the bin content to the current average is larger than for example five times of the current deviation (i.e., corresponding to a 5σ effect), the procedure terminates and the signal value, associated with the lower bound of the bin tested, is assigned to the threshold. The starting point in this scheme is assumed with the average and standard deviation as calculated from the first ten bins; the eleventh bin is the first one to be tested for a possible deviation from constancy.

Figure 6:
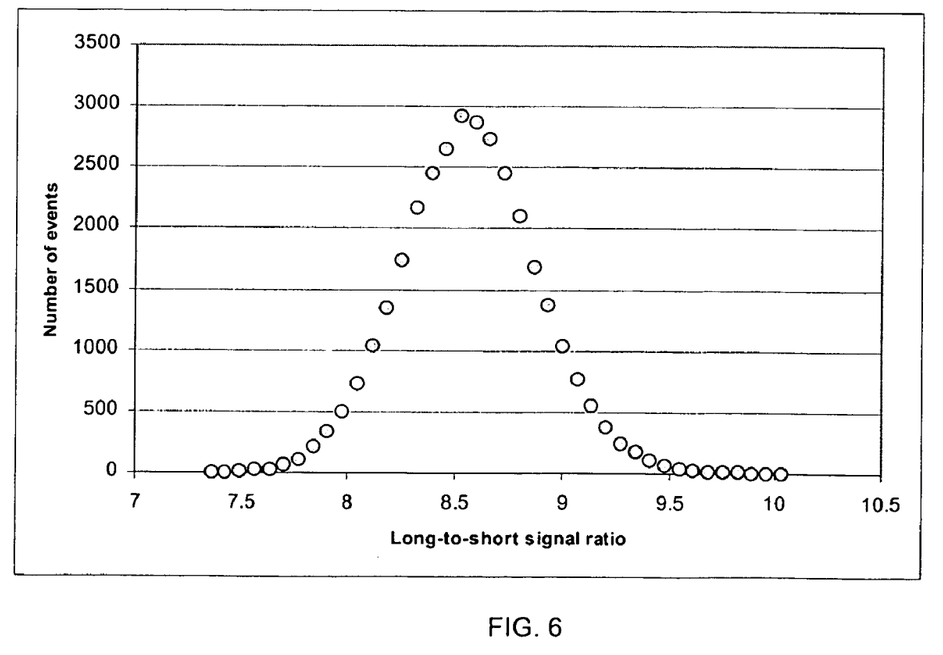
FIG. 6 is a plot showing distribution of signal ratios for pixels unsaturated by the long pulse dose in accordance with one embodiment of the present invention.

FIG. 6 shows an exemplary distribution of the signal ratios for all pixels unsaturated by long pulse dose. To avoid including defective pixels in the determination of the threshold, all signal ratios above 100 are ignored in FIGS. 5 and 6. By way of example, the optimal ratio in FIG. 6 is approximately 8.5.

Figure 7:
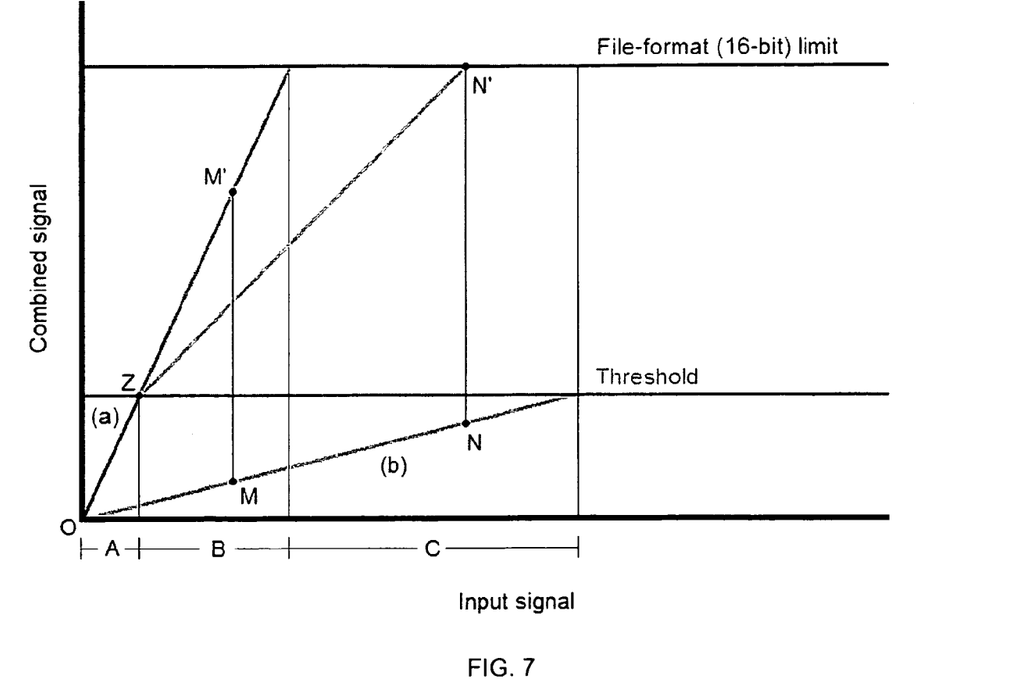
FIG. 7 is a plot showing computation of a combined image using data from long and short pulse images in accordance with one embodiment of the present invention.

FIG. 7 illustrates an exemplary dual pulse imaging method for generating a combined image with enhanced dynamic range. A first loop over the data defines the maximal (scaled) signal where the short pulse information is used. If this value is above the file format limit used in a data acquisition system such as 16-bit limit (i.e., 65535), a new ratio will be calculated and applied in order to avoid file format saturation. In this case, the maximal value is put equal to the limit such as 65535.

In FIG. 7, the long pulse signal (line (a)) is to be used in area A where the pixel values are lower than the threshold as determined above in connection with FIGS. 4-6. The short pulse signal (line (b)) is used in areas B and C where the long pulse signal can not be used. By dividing the file format limit (such as 16 bit) by the ratio (as obtained in connection with FIGS. 3-6), the maximal short pulse pixel value, which is denoted as v, can be determined that does not lead to file format saturation in the combined image. The maximal value actually present in the image may be lower (area B) or larger (area C) than the value of v. In the former case, e.g., the maximal value being represented by point M, the combined image is constructed on the basis of the straight line OM' where in the first segment (OZ) the long pulse pixel values are used, whereas in the second segment (MZ') the short pulse pixel values are used, scaled by an optimal ratio as described in connection with FIGS. 3-6. Evidently, the dynamic range of the combined image is larger than the one corresponding only to the long pulse information, yet it does not cover the entire interval up to the file format limit such as 16-bit. If, on the other hand, the maximal short pulse pixel value found in the image falls within area C, e.g., in the case of point N in FIG. 7, then the combined signal corresponds to two line segments: OZ where the long pulse information is used and ZN' where the short pulse information is used. This is done in order to avoid the file format saturation that would have been otherwise encountered for all those short pulse pixel values that are contained in area C. In this case, the dynamic range corresponds to the entire file format interval such as 16-bit.

EXAMPLES

The following example is provided to illustrate the invention and is not intended to limit the scope of the invention in any way.

Referring to FIG. 1, 25 tissue-equivalent phantom blocks 13, each of 2 cm thickness, were placed between the x-ray source 11 and detector 12. These blocks were set up in wedge steps and adjusted to the iso-center of the imaging system 10. Thus, a tissue equivalent of 50 cm having 2 cm attenuation variation were set up on the iso-center of the imaging system 10. An anti-scatter grid was used and the beam was collimated to a typical clinical field size of 10 cm×20 cm. Images were studied for peak tube voltages from 70 kVp to 125 kVp and exposures from 0.1 to 20 mAs.

A flat panel solid state imager PaxScan 4030CB, available from Varian Medical Systems, Inc. in Palo Alto, Calif., was used as detector 12. The imager features a pixel pitch of 194 μm and an active surface of 40×30 cm$^2$.

Two pulses of exposure corresponding 0.5 and 5 mAs were sequentially emitted to phantom blocks 13. To reach the imager 12 under the phantom blocks 13, some portions of the x-ray beam passed through only one phantom block while some portions of the x-ray beam passed through more or all blocks.

Contrast was quantified by the difference in pixel value of the images of two adjacent steps. Rectangular regions of interest of roughly 1000 pixels were chosen.

Figure 8:
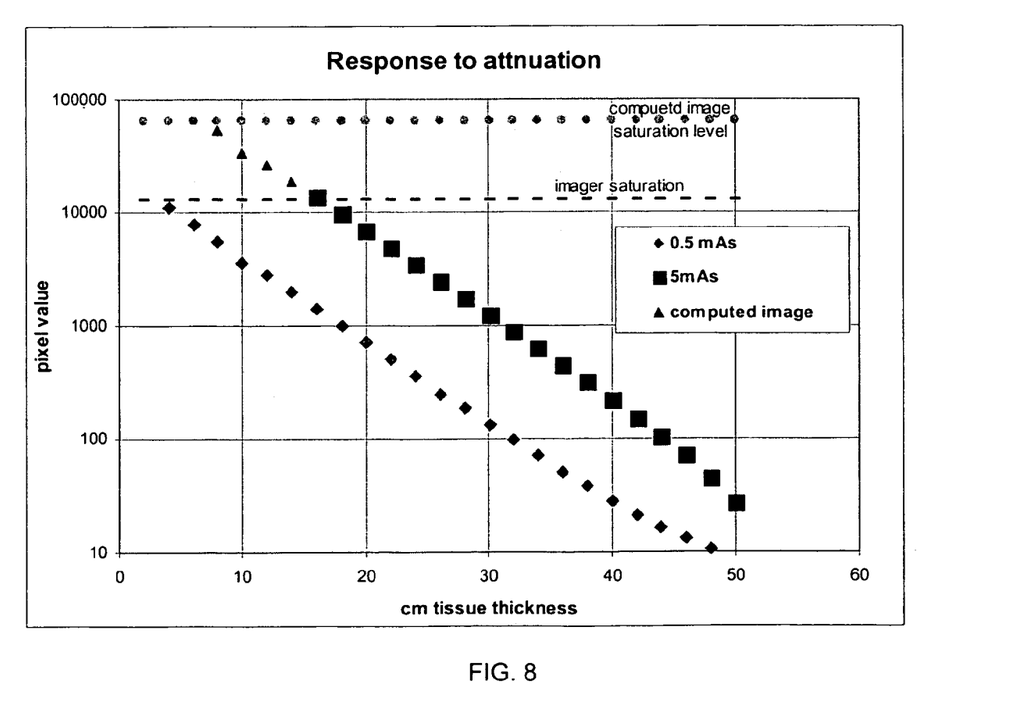
FIG. 8 is a plot showing dynamic ranges of signals of long pulse, short pulse and combined images in accordance with one embodiment of the present invention.

As shown in FIG. 8, the short pulse image had well-defined pixel values for thin tissue and air. The image contrast, however, was poor for tissues thicker than 36 cm; the standard deviation of the mean pixel values was of the same size as the difference between pixel values of two adjacent steps. The long pulse setting, on the other hand, allowed the steps until 50 cm tissue thickness to be imaged with high contrast. However, for tissues thinner than 14 cm, the signal is saturated. The method of the present invention was used to process the two images to generate a computed image. For the image computation, the information from pixels saturated by long pulse was not used, but it was replaced by the information acquired in the short pulse image. In this way the dynamic range increased from $2^{14}$ to $2^{16}$.

Figure 9:
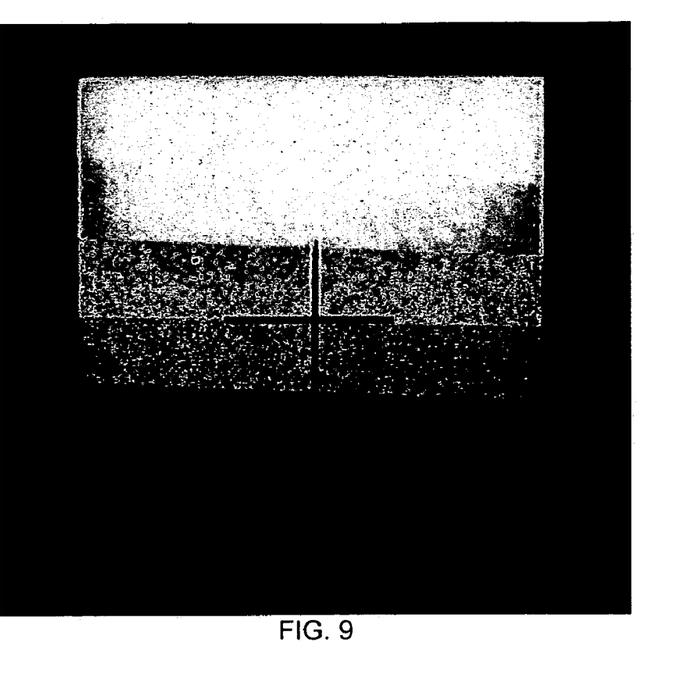
FIG. 9 is a radiographic image obtained by a long pulse exposure in accordance with one embodiment of the present invention.
Figure 10:
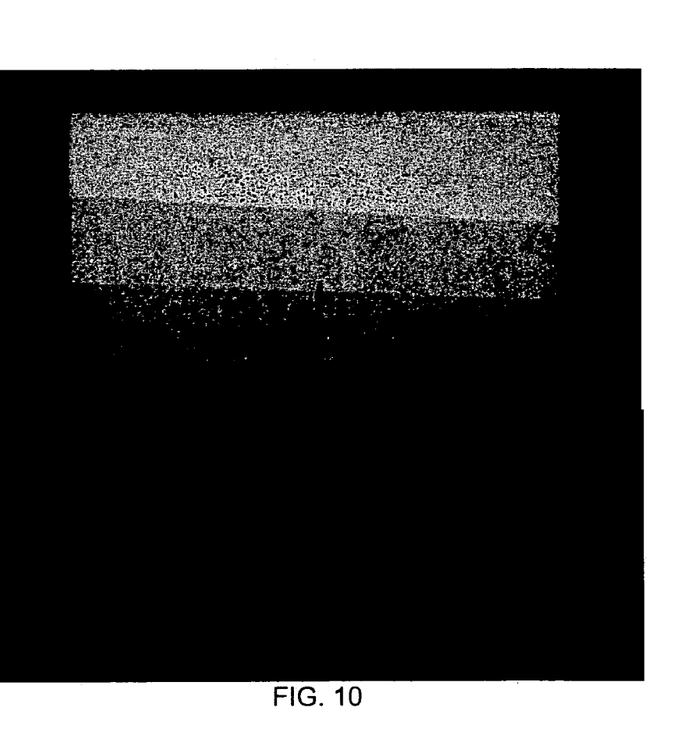
FIG. 10 is a radiographic image generated by the dual pulse imaging method in accordance with one embodiment of the present invention.

FIG. 9 is a radiographic image obtained by the long pulse x-ray. FIG. 10 is a radiographic image generated by using data from both the long and short pulses using the present method. As shown in FIG. 9, some regions (the light area) are saturated, where the phantom steps are not distinguishable; this corresponds to a tissue thickness of 0 to 14 cm. FIG. 10 shows that all steps of the thin tissue region are visualized.

The dual pulse imaging method of the present invention greatly enhances the dynamic range of the output signal, and generates images that retain the quality of the long pulse image in the high-attenuation areas and the details of the short pulse image in medium- and low-attenuation regions. The dual pulse imaging method can be advantageously used in both radiotherapy simulation and real therapy.

From the foregoing it will be appreciated that, although specific embodiments of the invention have been described herein for purposes of illustration, various modifications may be made without deviating from the spirit and scope of the invention.

What is claimed is:

1. A method of dual pulse imaging, comprising the steps of:
generating a first image of a region of interest by a first radiation pulse;
generating a second image of the region of interest by a second radiation pulse having higher tissue penetration properties than the first radiation pulse;
computing a third image of the region of interest using data from the first and second images;
wherein the first and second images are generated by an imager having a plurality of pixels;
wherein the step of computing the third image further comprising the step of identifying a threshold by determining ratios of pixel signals corresponding to the first and second radiation pulses, the threshold being used to determine data from the first and second images to be used in computing the third image.

2. The method of claim 1 farther comprising the step of determining an average value of the signal ratios for a number of values and comparing a signal ratio of a pixel with the average value.

3. The method of claim 1 further comprising grouping the signal ratios and determining an average ratio for each group.

4. The method of claim 1 further comprising the step of determining an optimal ratio of signals corresponding to the second and first radiation pulses reaching pixels unsaturated by the second pulse.

5. The method of claim 4 wherein the third image is computed by using data from the second image for pixels unsaturated by the second radiation pulse, and using data from the first image for pixels saturated by the second radiation pulse, said data from the first image being scaled by the optimal ratio.

6. A method of dual pulse imaging using an imager having a plurality of pixels, comprising the steps of:
generating a first image of a region of interest by a first radiation pulse;
generating a second image of the region of interest by a second radiation pulse having higher tissue penetration properties than the first radiation pulse;
identifying a threshold by determining ratios of pixel signals corresponding to the first and second radiation pulses;
determining whether one or more pixels are saturated by the second pulse passing through the region of interest based on the threshold;
computing a third image of the region of interest by using data from the second image for pixels unsaturated by the second pulse and data from the first image for pixels saturated by the second pulse.

7. The method of claim 6 wherein the data from the first image for computing the third image is scaled by a ratio of signals corresponding to the second and first radiation pulses for pixels unsaturated by the second pulse.

8. The method of claim 7 wherein the determining step comprises determining an average value of the ratios of signals corresponding to the second and the first radiation pulses for a definite number of pixels and comparing a signal ratio of a pixel with the average value.

9. A dual imaging system, comprising:
an energy source adapted to generate a first radiation pulse and a second radiation pulse having higher tissue penetration properties than the first radiation pulse;
a detector having a plurality of pixels generating a first image representative of the first pulse passing through a region of interest and a second image representative of the second pulse passing through the region of interest;
a memory storing said first and second images;
a processor processing the first and second images, identifying a threshold by determining ratios of pixel signals corresponding to the first and second radiation pulses, determining whether one or more pixels are saturated by the second pulse passing through the region of interest based on the threshold, and computing a third image using data from the first and second images;
wherein the third image is computed using data from the second image for pixels unsaturated by the second radiation pulse and data from the first image for pixels saturated by the second radiation pulse.

10. The system of claim 9 wherein the energy source is an X-ray source adapted to deliver sequential pulses of X-ray.

11. The system of claim 9 wherein the data from the first image is scaled by an average ratio of signals corresponding to the second and first radiation pulses for pixels unsaturated by the second radiation pulse.

* * * * *